(12) United States Patent
Zhang

(10) Patent No.: US 6,624,290 B2
(45) Date of Patent: Sep. 23, 2003

(54) AZAPEPTIDES USEFUL IN THE TREATMENT OF HEPATITIS C

(75) Inventor: Rumin Zhang, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/777,785

(22) Filed: Feb. 6, 2001

(65) Prior Publication Data

US 2002/0103135 A1 Aug. 1, 2002

Related U.S. Application Data

(60) Provisional application No. 60/181,017, filed on Feb. 8, 2000.

(51) Int. Cl.[7] ................................................. C07K 7/00
(52) U.S. Cl. ...................... 530/330; 530/329; 530/331; 514/16; 514/17
(58) Field of Search ................................ 530/329, 330, 530/331; 514/17, 16

(56) References Cited

FOREIGN PATENT DOCUMENTS

| EP | 0672678 A1 | 9/1995 |
|----|------------|--------|
| WO | WO 93/12078 | 6/1993 |

OTHER PUBLICATIONS

Gupton, B.F. et al., "Reaction of Azapeptides with Chymotrypsin-like Enzymes. New Inhibitors and Active Site Titrants for Chymotrypsin $A_a$ Subtilisin BPN', Subtilisin Carlsberg, and Human Leukocyte Cathepsin G", *The Journal of Biological Chemistry*, 259 (7):4279–4287 (Apr. 10, 1984).

Powers, J.C. et al., "Reaction of Azapeptides with Human Leukocyte Elastase and Porcine Pancreatic Elastase. New Inhibitors and Active Site Titrans", *The Journal of Biological Chemistry*, 259 (7):4288–4294 (Apr. 10, 1984).

Greenlee, W.J. et al., "Azapeptides: A New Class of Angiotensin–Converting Enzyme Inhibitors", *Biochemical and Biophysical Research Communications*, 122 (2):791–797 (Jul. 31, 1984).

Yanting, H. et al., "Synthesis and Testing of Azaglutamine Derivatives as Inhibitors of Hepatitis A Virus 3C Proteinase", *Bioorganic & Medicinal Chemistry*, vol. 7, pp. 607–619 (1999).

*Primary Examiner*—Christopher S. F. Low
*Assistant Examiner*—David Lukton
(74) *Attorney, Agent, or Firm*—Palaiyur S. Kalyanaraman; Margaret M. Albanese

(57) ABSTRACT

The present invention relates to azapeptide compounds represented by the formula:

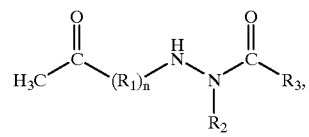

pharmaceutical compositions containing such compounds, and the use thereof in the treatment of Hepatitis C viral infections.

43 Claims, No Drawings

AZAPEPTIDES USEFUL IN THE TREATMENT OF HEPATITIS C

This application claims the benefit of Provisional Application No. 60/181,017, filed Feb. 8, 2000.

FIELD OF THE INVENTION

The present invention relates to novel azapeptide compounds, compositions comprising such compounds and methods of using them for the treatment of Hepatitis C Viral infections.

BACKGROUND OF THE INVENTION

Infection by hepatitis C virus ("HCV") is a compelling human medical problem. HCV is recognized as the causative agent for most cases of non-A, non-B hepatitis. Four million individuals may be infected in the United States alone.

WO 99/07734 assigned to Boehringer Ingelheim discloses azapeptides which inhibit NS3 protease useful in treating Hepatitis C. WO 99/20272 assigned to Merck & Co., discloses azapeptides useful as cell adhesion inhibitors. U.S. Pat. No. 5,837,687 and U.S. Pat. No. 5,965,538 both assigned to Fujirebro, disclose bicyclic ring azapeptides. WO 99/40063 assigned to Yoshitomi, discloses azapeptides having hydroxamic acid derivatives.

The HCV genome encodes a polyprotein of 3010–3033 amino acids [Choo, Q. -L., et al. "Genetic Organization and Diversity of the Hepatitis C Virus," *Proc. Natl. Acad. Sci. USA*, 88, pp. 2451–2455 (1991); Kato, N. et al., "Molecular Cloning of the Human Hepatitis C Virus Genome From Japanese Patients with Non-A, Non-B Hepatitis," *Proc. Natl. Acad. Sci. USA*, 87, pp. 9524–9528 (1990); Takamizawa, A. et al., "Structure and Organization of the Hepatitis C Virus Genome Isolated From Human Carriers," *J. Virol.*, 65, pp. 1105–1113 (1991)]. The HCV nonstructural (NS) proteins are presumed to provide the essential catalytic machinery for viral replication. The NS proteins are derived by proteolytic cleavage of the polyprotein [Bartenschlager, R. et al., "Nonstructural Protein 3 of the Hepatitis C Virus Encodes a Serine-Type Proteinase Required for Cleavage at the NS3/4 and NS4/5 Junctions," *J. Virol.*, 67, pp. 3835–3844 (1993); Grakoui, A. et al. "Characterization of the Hepatitis C Virus-Encoded Serine Proteinase: Determination of Proteinase-Dependent Polyprotein Cleavage Sites", *J. Virol.*, 67, pp. 2832–2843 (1993); Grakoui, A. et al., "Expression and Identification of Hepatitis C Virus Polyprotein Cleavage Products," 1385–1395 (1993); Tomei, L. et al., "NS3 is a Serine Protease Required for Processing of Hepatitis C Virus Polyprotein," *J. Virol.*, 67, pp. 4017–4026 (1993)].

The HCV NS protein 3 (NS3) contains a serine protease activity that helps process the majority of the viral enzymes, and is thus considered essential for viral replication and infectivity. The first 181 amino acids of NS3 (residues 1027–1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics," *J. Virol.*, 68, pp. 8147–8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral polyprotein processing. HIV protease inhibitors, which inhibit viral protein processing, are potent antiviral agents in man, indicating that interrupting this stage of the viral life cycle results in therapeutically active agents. Consequently the HCV NS3 serine protease is an attractive target for drug discovery.

There is a need for new treatments and therapies for HCV infection. It is, therefore, an object of this invention to provide compounds useful in the treatment or prevention or amelioration of one or more symptoms of HCV infection.

It is a further object herein to provide methods of treatment or prevention of HCV.

A still further object of the present invention is to provide methods for modulating the activity of serine proteases, particularly the HCV NS3/NS4a serine protease, using the compounds provided herein.

SUMMARY OF THE INVENTION

The present invention relates to azapeptide compounds represented by the formula:

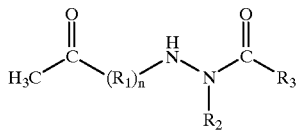

wherein:

(a) n 3–7;

(b) $R_1$=a substituted or unsubstituted amino acid or analog thereof;

(c) $R_2$=substituted or unsubstituted alkyl;
substituted or unsubstituted alkenyl;
substituted or unsubstituted heteroalkyl;
substituted or unsubstituted cycloalkyl;
substituted or unsubstituted aryl;
substituted or unsubstituted heteroaryl;
substituted or unsubstituted arylalkyl;
substituted or unsubstituted alkoxycarbonyl, or
substituted or unsubstituted aryloxycarbonyl;

(d) $R_3$=—O—CH($R_4$)—$R_5$; O—$R_5$, or S—$R_5$,
wherein $R_4$ is selected from the group consisting of:
H;
halo;
cyano;
substituted or unsubstituted alkyl, and
substituted or unsubstituted alkenyl;
and wherein $R_5$ is selected from the group consisting of:
substituted or unsubstituted alkyl;
substituted or unsubstituted haloalkyl;
substituted or unsubstituted haloalkenyl;
substituted or unsubstituted heteroalkyl;
substituted or unsubstituted cycloalkyl;
substituted or unsubstituted aryl;
substituted or unsubstituted heteroaryl, and
substituted or unsubstituted arylalkyl, or a pharmaceutically acceptable salt thereof.

The present invention further relates to a method of treating Hepatitis C comprising administering an effective amount of a compound having the formula:

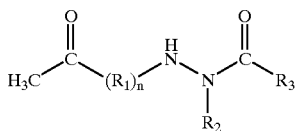

wherein:
(a) n=3–7;
(b) $R_1$=a substituted or unsubstituted amino acid or analog thereof;
(c) $R_2$=substituted or unsubstituted alkyl;
substituted or unsubstituted alkenyl;
substituted or unsubstituted heteroalkyl;
substituted or unsubstituted cycloalkyl;
substituted or unsubstituted aryl;
substituted or unsubstituted heteroaryl;
substituted or unsubstituted arylalkyl;
substituted or unsubstituted alkoxycarbonyl or
substituted or unsubstituted aryloxycarbonyl;
(d) $R_3$=—O—CH($R_4$)—$R_5$, —O—$R_5$, or —S—$R_5$,
wherein $R_4$ is selected from the group consisting of:
H;
halo;
cyano;
substituted or unsubstituted alkyl, and
substituted or unsubstituted alkenyl;
and wherein $R_5$ is selected from the group consisting of
substituted or unsubstituted alkyl;
substituted or unsubstituted alkenyl;
substituted or unsubstituted haloalkyl;
substituted or unsubstituted haloalkenyl;
substituted or unsubstituted heteroalkyl;
substituted or unsubstituted cycloalkyl;
substituted or unsubstituted aryl;
substituted or unsubstituted heteroaryl, and
substituted or unsubstituted arylalkyl,
or a pharmaceutically acceptable salt thereof.

DETAILED DESCRIPTION

The following definitions and terms are used herein:

The term "amino acid", as used herein, refers to organic compounds having the structure:

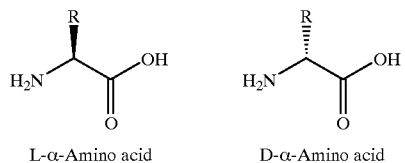

L-α-Amino acid     D-α-Amino acid

Amino acids useful in the present invention include, but are not limited to Alanine (Ala), Arginine (Arg), Asparagine (Asn), Aspartic Acid (Asp), Cysteine (Cys), Glutamic Acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), Valine (Val). Said amino acids can be substituted or unsubstituted. The amino acids can be in the D or L configuration in the present invention.

Amino acid analogs useful in the present invention include, but are not limited to, substituted proline, pipecolic acid, cyclohexylglycine, tert-butylglycine, D-γ-carboxyglutamic acid (D-Gla), and aminoadipic acid.

The term "peptide bond", as used herein, means the linkage that is formed between individual amino acids that is formed by the elimination of a molecule of water from the amino group of one amino acid and the carboxyl group of the next amino acid.

The term "heteroatom," as used herein, means a nitrogen, sulfur, or oxygen atom. Groups containing one or more heteroatoms may contain different heteroatoms.

The term "alkyl", as used herein, means an unsubstituted or substituted, straight or branched, saturated hydrocarbon chain. Said hydrocarbon chain having 1 to 8 carbon atoms, and preferably, unless otherwise stated, from 1 to 4 carbon atoms. Preferred alkyl groups include, but are not limited to, methyl, ethyl, propyl, isopropyl, and butyl.

The term "alkenyl" as used herein, means an unsubstituted or substituted, straight or branched hydrocarbon chain having at least one olefinic double bond. Said hydrocarbon chain having 2 to 8 carbon atoms, and preferably, unless otherwise stated, 2 to 4 carbon atoms.

The term "alkynyl" as used herein, means an unsubstituted or substituted straight or branched hydrocarbon chain having at least one triple bond.

The term "substituted", as used herein, means the replacement of one or more hydrogen radicals in a given structure with a radical selected from a specified group. When more than one hydrogen radical may be replaced with a substituent selected from the same specified group, the substituents may be either the same or different at every position.

The term "heteroalkyl", as used herein, means an unsubstituted or substituted, saturated chain having from 3 to 8-members and comprising carbon atoms and one or two hereroatoms.

The term "carbocyclic ring" or "carbocycle", as used herein, means an unsubstituted or substituted, saturated, unsaturated or aromatic, hydrocarbon ring. Carbocycles may be monocyclic or polycyclic: Monocyclic rings generally contain from 3 to 8 atoms, preferably 5 to 7 atoms. Polycyclic rings containing two rings, contain 6–16, preferably 10 to 12 atoms and those with three rings generally contain 13 to 17, preferably 14 to 15, atoms.

The terms "cycloalkyl" or "cycloalkane", alone or in combination with any other term, refers to a stable non-aromatic 3-to 8-membered carbon ring radical which is saturated and which may be optionally fused, for example benzofused, with one to three cycloalkyl, aromatic, heterocyclic or heteroaromatic rings. The cycloalkyl may be attached at any endocyclic carbon atom which results in a stable structure. Preferred carbocycles have 5 to 6 carbons. Examples of carbocycle radicals include, but are not limited to, cyclopropyl, cyclobutyl, cyclopentyl, cyclohexyl, cycloheptyl, cyclopentenyl, cyclohexenyl, indane, tetrahydronaphthalene and the like. Said carbocycles may be substituted or unsubstituted.

The term "heterocyclic ring" or "heterocycle", as used herein, means is an unsubstituted or substituted, saturated, unsaturated or aromatic ring comprised of carbon atoms and one or more heteroatoms in the ring. Heterocyclic rings may be monocyclic or polycyclic. Monocyclic rings generally contain from 3 to 8 atoms, preferably 5 to 7 atoms. Polycyclic ring systems consisting of two rings generally contain 6 to 16, preferably from 10 to 12 atoms. Polycyclic ring systems consisting of three rings generally contain 13 to 17 atoms, preferably 14 to 15 atoms. Each heterocyclic ring must have at least one nitrogen atom. Unless otherwise stated the heteroatoms may be independently chosen from nitrogen, sulfur and oxygen.

The term "aryl", as used herein, means a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two or three substitutents independently selected from lower alkyl, haloalkyl, alkoxy, amino, alkylamino, dialkylamino, hydroxy, halo, and nitro. In addition, substituted aryl groups include tetrafluorophenyl and pentafluorophenyl.

The term "heteroaryl", as used herein, means a mono- or bi-cyclic ring system containing one or two aromatic rings and containing at least one nitrogen, oxygen, or sulfur atom in an aromatic ring. Heteroaryl groups (including bicyclic heteroaryl groups) can be unsubstituted or substituted with one, two or three substituents independently selected from lower alkyl, haloalkyl, alkoxy, amino, alkylamino, dialkylamino, hydroxy, halo and nitro. Examples of heteroaryl groups include but are not limited to pyridine, pyrazine, pyrimidine, pyridazine, pyrazole, triazole, thiazole, isothiazole, benzothiazole, benzoxazole, thiadiazole, oxazole, pyrrole, imidazole and isoxazole.

The term "alkoxy", as used herein, means an oxygen atom having a hydrocarbon chain substituent, where the hydrocarbon chain is an alkyl or alkenyl (e.g.,—O-alkyl or —O-alkenyl). Preferred alkoxy groups include, but are not limited to, methoxy, ethoxy, propoxy, and alkyloxy.

The term "hydroxyalkyl", as used herein, means a substituted hydrocarbon chain which has a hydroxy substitutent (e.g., —OH), and may have other substituents. Preferred hydroxyalkyl groups include, but are not limited to, hydroxyethyl and hydroxypropyl.

The term "carboxyalkyl", as used herein, means a substituted hydrocarbon chain which has a carboxy substituent (e.g.,—COOH) and may have other substituents. Preferred carboxyalkyl groups include carboxymethyl, carboxyethyl, and their acids and esters.

The term "aminoalkyl", as used herein, means a hydrocarbon chain (e.g. alkyl) substituted with an amino moiety (e.g., NH-alky-), such as aminomethyl alkyl.

The term "alkylamino", as used herein, means an amino moiety having one or two alkyl substituents (e.g.,—N-alkyl), such as dimethylamino.

The term "alkylimino", as used herein, means an imino moiety having one or two alkyl substituents (e.g., -alkyl-N=).

The term "arylalkyl", as used herein, means an alkyl moiety substituted with an aryl group. Preferred arylalkyl groups include benzyl and phenylethyl.

The term "aroyl", as used herein, means the radical ArCO; wherein Ar is an aromatic group. Representative aroyls are benzoyl and naphthoyl.

The term "arylamino", as used herein, means an amine moiety substituted with an aryl group (e.g., aryl-NH—).

The term "aryloxy", as used herein, means an oxygen atom having an aryl substituent (e.g., aryl-O—).

The term "acyl", as used herein, means a carbon to oxygen double bond, e.g., R—CO. Preferred acyl groups include, but are not limited to, acetyl, propionyl, butanoyl and benzoyl.

The term "acyloxy", as used herein, means an oxygen atom having an acyl substituent (e.g., acyl-O—); for example, alkyl-C(=O)O.

The term "acylamino", as used herein, means an amino moiety having an acyl substituent (e.g., acyl-N—); for example, R—(C=O)—NH—.

The term "halo", "halogen atom", as used herein, means a chloro, bromo, fluoro, or iodo atom radical. Chloro, bromo, and fluoro are preferred halogen atoms.

The term "pharmaceutically-acceptable" salt, as used herein, means a cationic salt formed at any acidic (e.g., carboxyl group), or an anionic salt formed at any basic (e.g., amino) group. Many such salts known in the art, are described in World Patent Publication 87/05297, Johnston et al., published Sep. 11, 1987. Preferred cationic salts include the alkali-metal salts (such as sodium and potassium), and alkaline earth metal salts (such as magnesium and calcium). Preferred anionic salts include the halides (such as chloride), acetate and phosphate salts.

The term "pharmaceutical composition", as used herein, means a combination of an effective amount of the azapeptide compound of the present invention or mixtures thereof, and at least one pharmaceutically acceptable excipient.

The phrase "an effective amount", as used herein, means a therapeutically effective amount of a compound or composition large enough to modify the symptoms and/or condition to be treated, but small enough to avoid serious side effects (at a reasonable benefit/risk ratio), within the scope of sound medical judgment. The effective amount of active ingredient for use in the pharmaceutical compositions and the methods of the invention herein will vary depending upon the severity of the HCV infection, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients", as used herein, includes any physiologically inert, pharmacologically inactive material known to one skilled in the art, which is compatible with the physical and chemical characteristics of the particular azapeptide compound active ingredient selected for use. Pharmaceutically-acceptable excipients include, but are not limited to, polymers, resins, plasticizers, fillers, binders, lubricants, glidants, disintegrates, solvents, co-solvents, buffer systems, surfactants, preservatives, sweetening agents, flavoring agents, pharmaceutical grade dyes or pigments, and viscosity agents.

The term "oral dosage form", as used herein, means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection", as used herein, means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

The present invention relates to azapeptide compounds represented by the formula:

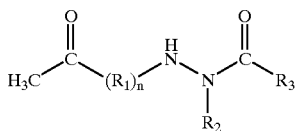

wherein:
(a) n 3–7;
(b) $R_1$=a substituted or unsubstituted amino acid or analog thereof;
(c) $R_2$=substituted or unsubstituted alkyl;
   substituted or unsubstituted alkenyl;
   substituted or unsubstituted heteroalkyl;
   substituted or unsubstituted cycloalkyl;
   substituted or unsubstituted aryl;
   substituted or unsubstituted heteroaryl;
   substituted or unsubstituted arylalkyl;
   substituted or unsubstituted alkoxycarbonyl or
   substituted or unsubstituted aryloxycarbonyl;
(d) $R_3$=—O—CH($R_4$)—$R_5$, —O—$R_5$, or —S—$R_5$,
   wherein $R_4$ is selected from the group consisting of:
   H;
   halo;
   cyano;
   substituted or unsubstituted alkyl, and
   substituted or unsubstituted alkenyl;
   and wherein $R_5$ is selected from the group consisting of
   substituted or unsubstituted alkyl;
   substituted or unsubstituted alkenyl;
   substituted or unsubstituted haloalkyl;
   substituted or unsubstituted haloalkenyl;
   substituted or unsubstituted heteroalkyl;
   substituted or unsubstituted cycloalkyl;
   substituted or unsubstituted aryl;
   substituted or unsubstituted heteroaryl, and
   substituted or unsubstituted arylalkyl,
or a pharmaceutically acceptable salt thereof.

The present invention further relates to a method of treating Hepatitis C comprising administering to a patient an effective amount (i.e. a therapeutically effective amount) of a compound having the formula:

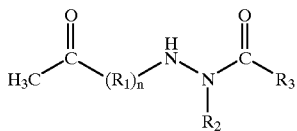

wherein:
(a) n=3–7;
(b) $R_1$=a substituted or unsubstituted amino acid or analog thereof;
(c) $R_2$=a substituted or unsubstituted alkyl;
   substituted or unsubstituted alkenyl;
   substituted or unsubstituted heteroalkyl;
   substituted or unsubstituted cycloalkyl;
   substituted or unsubstituted aryl;
   substituted or unsubstituted heteroaryl;
   substituted or unsubstituted arylalkyl;
   substituted or unsubstituted alkoxycarbonyl or
   substituted or unsubstituted aryloxycarbonyl;
(d) $R_3$=—O—CH($R_4$)—$R_5$, —O—$R_5$, or —S—$R_5$,
   wherein $R_4$ is selected from the group consisting of:
   H;
   halo;
   cyano;
   substituted or unsubstituted alkyl, and
   substituted or unsubstituted alkenyl;
   and wherein $R_5$ is selected from the group consisting of
   substituted or unsubstituted alkyl;
   substituted or unsubstituted alkenyl;
   substituted or unsubstituted haloalkyl;
   substituted or unsubstituted haloalkenyl;
   substituted or unsubstituted heteroalkyl;
   substituted or unsubstituted cycloalkyl;
   substituted or unsubstituted aryl;
   substituted or unsubstituted heteroaryl, and
   substituted or unsubstituted arylalkyl,
or a pharmaceutically acceptable salt thereof.

Preferably, in the formulas shown above, n is 3–7, more preferably n is 4–7 yet most preferred, n is 5.

$R_1$ is a substituted or unsubstituted amino acid or analog thereof. Preferably said amino acid is selected from the group consisting of Alanine (Ala), Arginine (Arg), Asparagine (Asn), Aspartic Acid (Asp), Cysteine (Cys), Glutamic Acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), Valine (Val) and analogs thereof. Most preferably said amino acid is selected from the group consisting of: Pro, Val, Glu, and analogs thereof. Preferred analogs are substituted proline, pipecolic acid, cyclohexylglycine, tert-butylglycine, D-γ-carboxyglutamic acid (D-Gla), and aminoadipic acid.

Preferably $R_2$ is a substituted or unsubstituted alkyl, heteroalkyl, cycloalkyl, aryl, heteroaryl, arylalkyl, alkoxycarbonyl or aryloxycarbonyl. More preferably $R_2$ is a substituted or unsubstituted alkyl, substituted or unsubstituted heteroalkyl or substituted or unsubstituted cycloalkyl. Most preferred, $R_2$ is a substituted or unsubstituted lower alkyl, e.g. ethyl, n-propyl, n-butyl, allyl, and cyclopropylmethyl or heteroalkyl, e.g. methylsulfanylmethyl, ethylsulfanylmethyl and CN-methyl. Still more preferably $R_2$ is n-propyl or n-butyl.

$R_3$ is —O—CH($R_4$)—($R_5$); —O—$R_5$ or —S—$R_5$. Preferably $R_3$ is —O—CH($R_4$) ($R_5$), wherein, $R_4$ is selected from the group consisting of:
H;
halogen;
CN, and
alkyl,
and wherein $R_5$ is selected from the group consisting of:
substituted or unsubstituted alkyl;
substituted or unsubstituted haloalkyl, e.g. trichloromethyl;
substituted or unsubstituted heteroalkyl;
substituted or unsubstituted cycloalkyl;
substituted or unsubstituted aryl, (e.g. 2- or 4-nitrophenyl, 4-methoxycarbonylphenyl, 4-fluorophenyl, 4-chlorophenyl, or 4 methylphenyl);
substituted or unsubstituted heteroaryl, and
substituted or unsubstituted arylalkyl.

More preferably, $R_4$ is halogen e.g. bromo, chloro, iodo, or fluoro.

Preferably, $R_5$ is selected from substituted or unsubstituted alkyl, (e.g. methyl, ethyl, n-propyl or n-butyl) or substituted or unsubstituted haloalkyl, (e.g. trifluoromethyl, or trichloromethyl). More preferred, $R_5$ is substituted or unsubstituted haloalkyl, with trichloromethyl being the most preferred.

The following Examples further describe and demonstrate the preferred embodiments within the scope of the claimed invention. The following examples are given solely for the purpose of illustration, and are not to be construed as limitations of the present invention since many variations thereof are possible without departing from the spirit and scope of the invention.

EXAMPLE 1

N-[N-[N-[N-[N-[N-acetyl-L-aspartyl]-L-threonyl]-L-glutamyl]-L-aspartyl]-L-valyl]-L-valyl]-L-proline 2-[(4-nitrophenoxy)carbonyl]-2-propylhydrazine (SEQ. ID. NO.: 1)

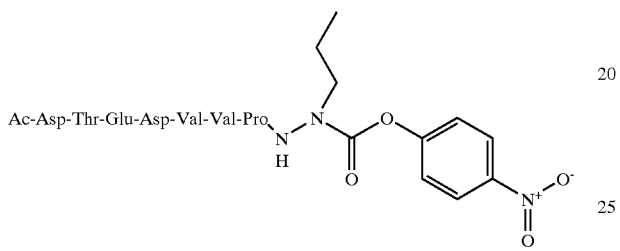

EXAMPLE 2

N-[N-[N-[N-[N-acetyl-L-glutamyl]D-γ-carboxyglutamyl]-L-valyl]-L-valyl]-L-proline 2-[(4-nitrophenoxy)carbonyl]-2-propylhydrazine (SEQ. ID. NO.: 2)

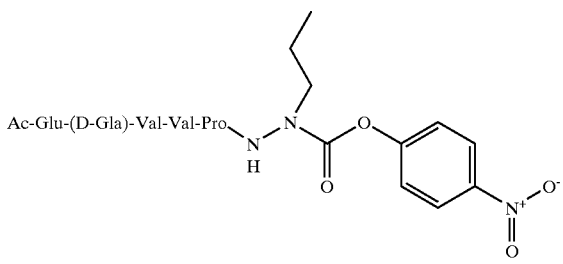

EXAMPLE 3

N-[N-[N-[N-[N-[N-acetyl-L-aspartyl]-L-threonyl]-L-glutamyl]-L-aspartyl]-L-valyl]-L-valyl]-L-proline 2-[(1,2,2,2-tetrachloroethoxy)carbonyl]-2-propylhydrazine (SEQ. ID. NO.: 3)

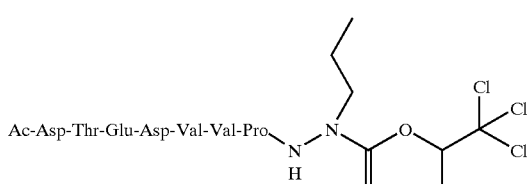

EXAMPLE 4

N-[N-[N-[N-[N-acetyl-L-glutamyl]-D-γ-carboxyglutamyl]-L-valyl]-L-valyl]-L-proline 2-[(1-chloro-2-methylpropyloxy)carbonyl]-2-propylhydrazine (SEQ. ID. NO.: 4)

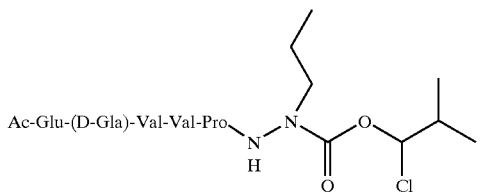

EXAMPLE 5

N-[N-[N-[N-[N-acetyl-L-glutamyl]-D-γ-carboxyglutamyl]-L-valyl]-L-Valyl]-L-proline 2-[(chloromethoxy)carbonyl]-2-propylhydrazine (SEQ. ID. NO.: 5)

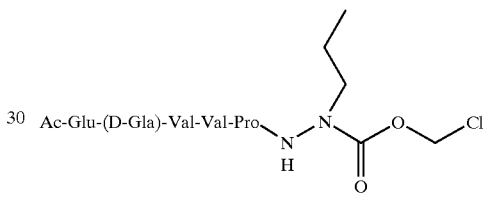

EXAMPLE 6

N-[N-[N-[N-[N-acetyl-L-glutamyl]-D-γcarboxglutamyl]L-valyl]-L-valyl]-L-proline 2-[(1,2,2,2tetrachloroethoxy)carbonyl]-2-propylhydrazine (SEQ. ID. NO.: 6)

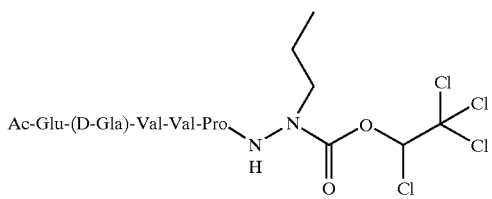

have Ki values of 0.03 $\mu$M and 0.05 $\mu$M, respectively.

Azapeptide Synthesis

Azapeptides were prepared using Fmoc-protected amino acid carbazate dipeptide synthons (following Quibell, M.; Trunell, W. G.; Johnson, T. J. Chem. Soc. Perkin Trans. 1, 1993, 2843), N1-(Fmoc-Prolyl)-N2-monoalkyl-hydrazine. Briefly, Fmoc-Pro-pentafluorophenyl ester was reacted quantitatively with hydrazine monohydrate (1 mol. equiv.) in dichloromethane to form Fmoc-Pro-NH—NH$_2$ followed by a two-step reductive alkylation (hydrazone formation with an appropriate aldehyde such as propionaldehye in dry THF overnight and then reduction by sodium cyanoborohydride in ethanol containing 1% acetic acid). The monoalkylated dipeptide synthon species was purified by FLASH chromatograhy and confirmed by mass and NMR analysis. The dipeptide synthon was first anchored to 2-chlorotrityl chloride resin (Barlos, K.; Chatzi, O.; Gatos, D.; Stavropoulos, G. Int. J. Peptide Protein Res. 1991, 37, 513) and the rest of the peptide sequence assembled on the solid support. The protected peptide segment was cleaved off the resin using 2% trifluoroacetic acid in dichloromethane for 10 min followed by acid extraction with sodium carbonate in brine and dried over sodium sulfate. Various commercial chloroformating agents (2 mol. equiv.) were reacted with the protected peptide hydrazides in dichloromethane in the presence of N-methylmorpholine (4 mol. equiv.). Examples of the chloroformating reagents included 4-nitrophenyl chloroformate (for compounds in Examples 1 and 2), 1,2,2,2-tetrachloroethyl chloroformate (for compounds in Examples 3 and 6), 1-chloro-2-methylpropyl chloroformate (for compound in Example 4), and chloromethyl chloroformate (for compound in Example 5). The reaction was quenched by 4% hydrochloride (aq.) and the dichloromethane phase was evaporated before final deprotection with 95% trifluoroacetic acid. The azapeptides were purified by HPLC and confirmed by mass spectroscopic analysis.

Administration and Dosage

The azapeptide compounds of the present invention may be administered to humans or other mammals by a variety of routes, including, but not limited to, topical, oral and parenteral (i.e. intravenous, intramuscular, intraperitoneal and subcutaneous injections) and dosage forms, including but not limited to those described in *Remington's Pharmaceutical Sciences,* 18th Ed., Mack Publishing Company, 1990 (i.e. liquids, suspensions and tablets). Numerous other dosage forms containing the novel ketoamide compounds of the present invention can be readily formulated by one skilled in the art, utilizing the suitable pharmaceutical excipients as defined below. For considerations of patient compliance, oral dosage forms are generally most preferred.

The rate of systemic delivery can be satisfactorily controlled by one skilled in the art, by manipulating any one or more of the following:

(a) the active ingredient proper;

(b) the pharmaceutically-acceptable excipients; so long as the variants do not interfere in the activity of the particular active ingredient selected;

(c) the type of the excipient, and the concomitant desirable thickness and permeability (swelling properties) of said excipients;

(d) the time-dependent conditions of the excipient itself and/or within the excipients;

(e) the particle size of the granulated active ingredient; and (f) the pH-dependent conditions of the excipients.

Depending upon their structure, the compounds of the invention may form pharmaceutically acceptable salts with organic or inorganic acids, or organic or inorganic bases. Examples of suitable acids for such salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. For formation of salts with bases, suitable bases are, for example, NaOH, KOH, NH$_4$OH, tetraalkylammonium hydroxide, and the like.

In another embodiment, this invention provides pharmaceutical compositions comprising the inventive peptides as an active ingredient. The pharmaceutical compositions generally additionally comprise a pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include but are not limited to starch, gelatin, natural sugars, corn sweeteners, natural and synthetic gums such as acacia, sodium alginate, carboxymethylcellulose, polyethylene glycol and waxes.

Among the lubricants, there may be mentioned for use in these dosage forms, boric acid, sodium benzoate, sodium acetate, sodium chloride, and the like.

Disintegrants include starch, methylcellulose, guar gum and the like.

Sweetening and flavoring agents and preservatives that may be added where appropriate include but are not limited to those described in *Remington's Pharmaceutical Sciences,* 18th Ed., Mack Publishing Company, 1990, pp. 1288–1300.

Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally, intravenously or subcutaneously.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients among those useful herein include those described in Handbook of Pharmaceutical Excipients, pp. 81090, 1986 by the American Pharmaceutical Association & the Pharmaceutical Society of Great Britian, incorporated by reference herein as well as other food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, hepatitis C and the like. The method comprises administering a therapeutically effective amount of the inventive pharmaceutical composition to a patient having such a disease or diseases and in need of such a treatment.

In yet another embodiment, the compounds of the invention may be used for the treatment of HCV in humans in monotherapy mode or in a combination therapy mode such as, for example, in combination with antiviral agents such as, for example, ribavirin and/or interferon such as, for example, interferon-alfa, amantadine, pegylated interferon-alfa and the like.

The term "interferon-alfa" as used herein means the family of highly homologous species-specific proteins that inhibit viral replication and cellular proliferation and modulate immune response. Typical suitable interferon-alfas include, but are not limited to, recombinant interferon alfa-2b such as Intron-A interferon available from Schering Corporation, Kenilworth, N.J., recombinant interferon alfa-2a such as Roferon interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alfa interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alfa-n3 a mixture of natural alfa interferons made by Interferon Sciences and available from the Purdue Frederick Co., Norwalk, Conn., under the Alferon Tradename. The use of interferon alfa-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,530,901.

The term "pegylated interferon alfa" as used herein means polyethylene glycol modified conjugates of interferon alfa, preferably interferon alfa-2a and -2b. The preferred polyethylene-glycol-interferon alfa-2b conjugate is $PEG_{12000}$-interferon alfa 2b. The phrases "12,000 molecular weight polyethylene glycol conjugated interferon alpha" and "$PEG_{12000}$-IFN alfa" as used herein mean conjugates such as are prepared according to the methods of International Application No. WO 95/13090 and containing urethane linkages between the interferon alfa-2a or -2b amino groups and polyethylene glycol having an average molecular weight of 12000.

The preferred $PEG_{12000}$-interferon alfa-2b is prepared by attaching a PEG polymer to the epsilon amino group of a lysine residue in the IFN alfa-2b molecule. A single $PEG_{12000}$ molecule is conjugated to free amino groups on an IFN alfa-2b molecule via a urethane linkage. This conjugate is characterized by the molecular weight of $PEG_{12000}$ attached. The PEG12000-IFN alfa-2b conjugate is formulated as a lyophilized powder for injection. The objective of conjugation of IFN alfa with PEG is to improve the delivery of the protein by significantly prolonging its plasma half-life, and thereby provide protracted activity of IFN alfa.

Other interferon alfa conjugates can be prepared by coupling an interferon alfa to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alfa-polymer conjugates are described in U.S. Pat. No. 4,766,106, U.S. Pat. No. 4,917,888, European Patent Application No. 0 236 987, European Patent Application Nos. 0510 356, 0 593 868 and 0 809 996 (pegylated interferon alfa-2a) and International Publication No. WO 95/13090.

Pharmaceutical composition of pegylated interferon alfa-suitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human plasma albumin), toxicity agents (e.g. NaCl), preservatives (e.g. thimerosol, cresol or benylalcohol), and surfactants(e.g. tween or polysorabates) in sterile water for injection. The pegylated interferon alfa-may be stored as lyophilized powders under a refrigeration at 2°–8° C. The reconstituted aqueous solutions are stable when stored between 2° and 8° C. and used within 24 hours of reconstitution. See for example U.S. Pat. Nos., 4,492,537; 5,762,923 and 5,766,582. The reconstituted aqueous solutions may also be stored in prefilled, multi-dose syringes such as those useful for delivery of drugs such as insulin. Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized pegylated interferon-alfa powder in a separate compartment.

In a further embodiment, the compounds of the invention may be used for the treatment of HCV in humans in combination therapy mode with other inhibitors of HCV protease.

In yet a further embodiment, the compounds of the invention may be used for the treatment of HCV in humans in combination therapy mode with other enzyme inhibitors in the HCV life cycle such as, for example, inhibitors of HCV helicases, inhibitors of HCV RNA polymerases, and/or inhibitors of HCV metalloproteases.

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

The preferred pharmaceutically acceptable carrier is purified water.

Preferred co-solvents with water include, but are not limited to, ethanol, glycerin, propylene glycol, polyethylene glycols. The pharmaceutical compositions of the present invention include from 0–50% by weight of at least one co-solvent.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. More preferred buffer systems are phosphoric, tartaric, citric, and acetic acids and salts. The pharmaceutical composition of the present invention generally contain from 0–5% by weight, buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical composition of the present invention generally contain from 0–2% by weight surfactants.

Preferred pharmaceutically acceptable preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. More preferred are the salts of benzoic acid, cetylpyridinium chloride, methyl paraben and propyl paraben. The compositions of the present invention generally include from 0–2% by weight preservatives.

Pharmaceutically acceptable fillers include, but are not limited to, lactose, mannitol, sorbitol, tribasic calcium phosphate, diabasic calcium phosphate, compressible sugar, starch, calcium sulfate, dextro and microcrystalline cellulose. The compositions of the present invention contain from 0–75% by weight fillers.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

When these compounds or their pharmaceutically acceptable salts are formulated together with a pharmaceutically acceptable carrier, the resulting composition may be administered in vivo to mammals, such as man, to inhibit serine proteases, particularly HCV NS3 protease or to treat or prevent viral infection, particularly HCV virus infection. Such treatment may also be achieved using the compounds of this invention in combination with agents which include, but are not limited to: immunomodulatory agents, such as α-, β-, or γ-interferons; other antiviral agents such as ribavirin, amantadine; other inhibitors of HCV N3 protease; inhibitors of other targets in the HCV life cycle such as helicase, polymerase, metalloprotease, or internal ribosome entry; or combinations thereof. These additional agents may be combined with the compounds of this invention to create a single dosage form. Alternatively these additional agents may be separately administered to a mammal as part of a multiple dosage form.

The pharmaceutically-acceptable carrier employed in conjunction with the compounds of the present invention is used at a concentration sufficient to provide a practical size to dosage relationship. The pharmaceutically-acceptable carriers, in total, may comprise from 0.1% to 99.9% by weight of the pharmaceutical compositions of the present invention, and preferably from 20% to 80% by weight.

Assays

The compounds of the invention were assayed according to the procedure described in Rumin Zhang et al, "A Continuous Spectrophotometric Assay for the Hepatitis C Virus Serine Protease", *Analytical Biochemistry,* Vol. 270, pp.268–275 (1999).

Compounds of the present invention exhibit HCV Serine protease inhibitory activity and have Ki values in the range of about 0.03 to about 100 μM in the above described assay. Preferred compounds of the invention have Ki values in the range of about 0.03 μM to about 9 μM.

Azapeptides

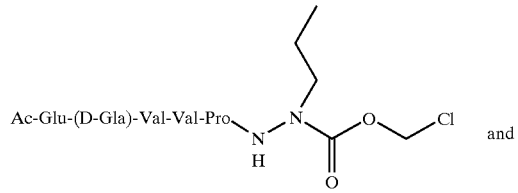

(SEQ. ID. NO.: 5)

and

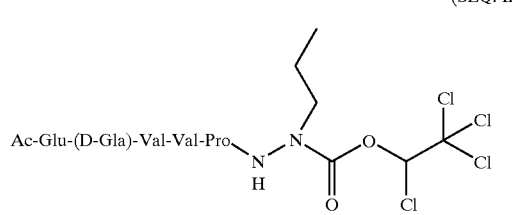

(SEQ. ID. NO.: 6)

have Ki values of 0.03 μM and 0.05 μM, respectively.

I claim:

1. An azapeptide compound represented by the formula:

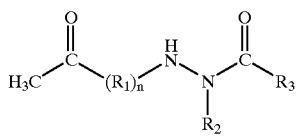

wherein:
(a) n=3–7
(b) $R_1$=a substituted or unsubstituted amino acid;
(c) $R_2$=substituted or unsubstituted alkyl;
  substituted or unsubstituted alkenyl;
  substituted or unsubstituted heteroalkyl;
  substituted or unsubstituted cycloalkyl;
  substituted or unsubstituted aryl;
  substituted or unsubstituted heteroaryl;
  substituted or unsubstituted arylalkyl;
  substituted or unsubstituted alkoxycarbonyl, or
  substituted or unsubstituted aryloxycarbonyl;
(d) $R_3$=—O—CH($R_4$)—$R_5$, —O—$R_5$, or —S—$R_5$,
  wherein $R_4$ is selected from the group consisting of:
    H;
    halo;
    cyano;
    substituted or unsubstituted alkyl, and
    substituted or unsubstituted alkenyl;
  and wherein $R_5$ is selected from the group consisting of unsubstituted or substituted alkyl, with the proviso that said substitution does not include fluorine as a substituent;
  substituted or unsubstituted alkenyl;
  substituted or unsubstituted haloalkyl;
  substituted or unsubstituted haloalkenyl;
  substituted or unsubstituted heteroalkyl;
  substituted or unsubstituted cycloalkyl;
  substituted or unsubstituted heteroaryl, and
  substituted or unsubstituted arylalkyl, with the proviso that when $R_2$ is a substituted alkyl, $R_5$ is not a substituted or unsubstituted arylalkyl,
or a pharmaceutically acceptable salt thereof.

2. The compound of claim 1, wherein n is 4–7.

3. The compound of claim 2, wherein n is 5.

4. The compound of claim 1, wherein $R_1$ is selected from the group consisting of:
  Pro;
  Val;
  Glu, and substituted analogs;
wherein said analogs are selected from the group consisting of:
  proline
  pipecolic acid;
  cyclohexylglycine;
  tert-butylglycine;
  D-γ-carboxyglutamic acid, and
  aminoadipic acid.

5. The compound of claim 4, wherein $R_1$ is selected from the group consisting of:
  Pro;
  Val;

Glu, and

D-γ-carboxyglutamic acid.

6. The compound of claim 1, wherein $R_2$ is selected from the group consisting of:

substituted or unsubstituted alkyl, and substituted or unsubstituted heteroalkyl.

7. The compound of claim 6, wherein $R_2$ is substituted or unsubstituted alkyl, or substituted or unsubstituted heteroalkyl.

8. The compound of claim 7, wherein $R_2$ is selected from the group consisting of:

ethyl;

n-propyl;

n-butyl;

allyl;

cyclopropylmethyl;

methylsulfanylmethyl;

ethylsulfanylmethyl, and cyanomethyl.

9. The compound of claim 8, wherein $R_2$ is selected from the group consisting of:

n-propyl, and n-butyl.

10. The compound of claim 1, wherein $R_3$ is selected from the group consisting of:

—O—CH($R_4$)—($R_5$), and

—S—$R_5$, and wherein, $R_4$ is selected from the group consisting of:

H;

halogen;

cyano;

alkyl, and alkenyl;

and wherein, $R_5$ is selected from the group consisting of:

unsubstituted or substituted alkyl, with the proviso that said substitution does not include fluorine as a substituent;

substituted or unsubstituted alkenyl;

substituted or unsubstituted haloalkyl, and substituted or unsubstituted haloalkenyl.

11. The compound of claim 10, wherein $R_3$ is —O—CH($R_4$)—($R_5$) and wherein $R_4$ is halogen and $R_5$ is selected from the group consisting of:

unsubstituted or substituted alkyl, with the proviso that said substitution does not include fluorine as a substituent;

substituted or unsubstituted alkenyl; and substituted or unsubstituted haloalkenyl.

12. The compound of claim 11, wherein $R_3$ is —O—CH($R_4$)—($R_5$); and wherein $R_4$ is selected from the group consisting of:

bromine;

chlorine iodine, and fluorine, and $R_5$ is selected from the group consisting of:

unsubstituted or substituted alkyl, with the proviso that said substitution does not include fluorine as a substituent;

substituted or unsubstituted alkenyl; and substituted or unsubstituted haloalkenyl.

13. The compound of claim 12, wherein $R_3$ is —O—CH($R_4$)—($R_5$); and wherein $R_4$ is selected from the group consisting of:

bromine;

chlorine iodine, and flourine, and where $R_5$ is from the group consisting of:

methyl ethyl;

n-propyl;

n-butyl; and trichlorometyl.

14. The compound of claim 13, wherein $R_3$ is —O—CH($R_4$)—($R_5$);

and wherein $R_4$ is selected from the group consisting of:

bromine;

chlorine iodine, and flourine, and wherein $R_5$ is trichloromethyl.

15. The compound of claim 1 wherein, n is 5, and $R_5$ is trichloromethyl.

16. A composition comprising a compound of claim 1 and a pharmaceutically acceptable carrier.

17. A method of inhibiting hepatitis C virus replication comprising administering an effective amount of a compound of claim 1 to a patient in need thereof.

18. A method of inhibiting hepatitis C virus replication comprising administering to a patient in need thereof an effective amount of a compound of claim 1 combination with an enzyme inhibitor.

19. The method of claim 18 wherein the enzyme inhibitor is selected from the group consisting of:

a) inhibitors of HCV helicases;

b) inhibitors of HCV RNA polymerases, and c) inhibitors of HCV metalloproteases.

20. A method of inhibiting hepatitis C virus replication comprising administering to a patient in need thereof an effective amount of a compound of claim 1 in combination with one or more antiviral agents.

21. The method of claim 20 wherein said one or more antiviral agents are ribavirin (1-β-D-Ribofuranosyl-1H-1,2, 4-triazole-3-carboxamide), amantadine or interferon.

22. The method of claim 21 wherein said interferon is selected from the group consisting of interferon-alfa, and pegylated interferon-alfa.

23. A compound selected from the group consisting of:

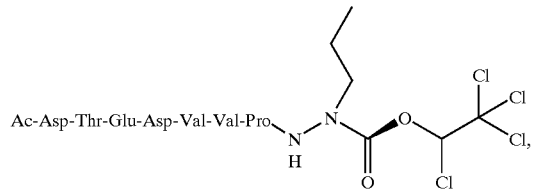

-continued

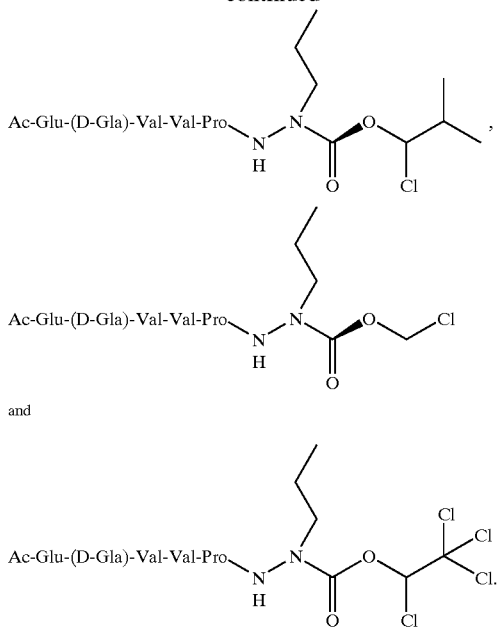

24. A method of inhibiting hepatitis C virus replication comprising administering to a patient in need thereof an effective amount of a compound of claim 23 in combination with an enzyme inhibitor.

25. A method of inhibiting Hepatitis C nonstructural protein-3 protease (HCV NS3 protease) in a patient in need of such inhibition comprising, administering an effective amount of any of the compounds of claim 23 in combination with one or more antiviral agents for a time and under conditions effective to inhibit HCV NS3 protease.

26. The method of claim 25 wherein said one or more antiviral agents are ribavirin (1-β-D-Ribofuranosyl-1H-1,2,4-triazole-3-carboxamide), amantadine or interferon.

27. The method of claim 26 wherein the interferon is selected from the group consisting of interferon-alfa, and pegylated interferon-alfa.

28. A method of inhibiting Hepatitis C virus nonstructural protein-3 protease (HCV NS3 protease) in a patient in need of said inhibition, comprising administering an effective amount of any of the compounds of claim 23 to said patient for a time and under conditions effective to inhibit HCV NS3 protease.

29. A composition comprising a pharmaceutically acceptable carrier in combination with any of the compounds of claim 23.

30. A method of inhibiting Hepatitis C virus nonstructural protein-3 protease (HCV NS3 protease) in a patient in need of said inhibition, comprising administering an effective amount of any of the compounds of claim 26 in combination with an enzyme inhibitor for a time and under conditions effective to inhibit HCV NS3 protease wherein the enzyme inhibitor is selected from the group consisting of:
  a) inhibitors of HCV helicases;
  b) inhibitors of HCV RNA polymerases, and
  c) inhibitors of HCV metalloproteases.

31. A compound of the formula:

(SEQ. ID. NO.: 5)

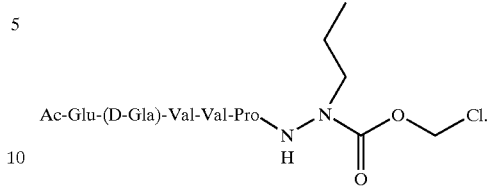

32. A method of inhibiting Hepatitis C virus nonstructural protein-3 protease (HCV NS3 protease) in a patient in need of said inhibition, comprising, administering an effective amount of the compound of claim 31 to said patient for a time and under conditions effective to inhibit HCV NS3 protease.

33. A method of inhibiting Hepatitis C virus nonstructural protein-3 protease (HCV NS3 protease) in a patient in need of said inhibition comprising, administering an effective amount of the compound of claim 31 in combination with one or more antiviral agents for a time and under conditions effective to inhibit HCV NS3 protease.

34. The method of claim 33 wherein said one or more antiviral agents are ribavirin (1-β-D-Ribofuranosyl-1H-1,2,4-triazole-3-carboxamide), amantadine or interferon.

35. The method of claim 34 wherein said interferon is selected from the group consisting of interferon-alfa, and pegylated interferon-alfa.

36. A composition comprising a pharmaceutically acceptable carrier and a compound of claim 31.

37. A compound of the formula:

(SEQ. ID. NO.: 6)

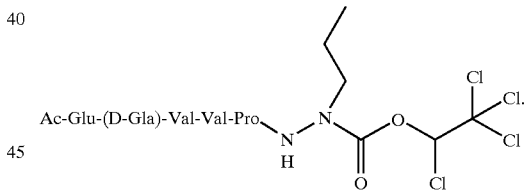

38. A method of inhibiting Hepatitis C virus nonstructural protein-3 protease (HCV NS3 protease) in a patient in need of said inhibition comprising, administering an effective amount of the compound of claim 37 to said patient for a time and under conditions effective to inhibit HCV NS3 protease.

39. A composition comprising a compound of claim 37 and a pharmaceutically acceptable carrier.

40. A method of inhibiting Hepatitis C virus nonstructural protein-3 protease (HCV NS3 protease) in a patient in need of said inhibition comprising, administering an effective amount of the compound of claim 37 in combination with one or more antiviral agents for a time and under conditions effective to inhibit HCV NS3 protease.

41. The method of claim 40 wherein said one or more antiviral agents are ribavirin (1-β-D-Ribofuranosyl-1H-1,2,4-triazole-3-carboxamide), amantadine or interferon.

42. The method of claim 41 wherein said interferon is selected from the group consisting of interferon-alfa, and pegylated interferon-alfa.

43. A method of inhibiting Hepatitis C virus nonstructural protein-3 protease (HCV NS3 protease) in a patient in need of said inhibition comprising, administering an effective amount of any of the compounds of claim 37 in combination with an enzyme inhibitor for a time and under conditions effective to inhibit HCV NS3 protease wherein the enzyme inhibitor is selected from the group consisting of:

a) inhibitors of HCV helicases;
b) inhibitors of HCV RNA polymerases, and
c) inhibitors of HCV metalloproteases.

* * * * *

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:azapeptide
<221> NAME/KEY: MOD_RES
<222> LOCATION: (1)
<223> OTHER INFORMATION: ACETYLATION
```

```
<221> NAME/KEY: UNSURE
<222> LOCATION: (7)
<223> OTHER INFORMATION: 2[(4-nitrophenoxy)carbonyl]-2-propylhydrazine

<400> SEQUENCE: 1

Asp Thr Glu Asp Val Val Pro
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:azapeptide
<221> NAME/KEY: MOD_RES
<222> LOCATION: (1)
<223> OTHER INFORMATION: ACETYLATION
<221> NAME/KEY: UNSURE
<222> LOCATION: (5)
<223> OTHER INFORMATION: 2-[(4-nitrophenoxy)carbonyl]-2-propylhydrazine
<221> NAME/KEY: UNSURE
<222> LOCATION: (2)
<223> OTHER INFORMATION: Xaa=D-gamma-carboxyglutamic acid

<400> SEQUENCE: 2

Glu Xaa Val Val Pro
 1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:azapeptide
<221> NAME/KEY: MOD_RES
<222> LOCATION: (1)
<223> OTHER INFORMATION: ACETYLATION
<221> NAME/KEY: UNSURE
<222> LOCATION: (7)
<223> OTHER INFORMATION: 2-[(1,2,2,2-tetrachloroethoxy)carbonyl]
      -2-propylhy drazine

<400> SEQUENCE: 3

Asp Thr Glu Asp Val Val Pro
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:azapeptide
<221> NAME/KEY: MOD_RES
<222> LOCATION: (1)
<223> OTHER INFORMATION: ACETYLATION
<221> NAME/KEY: UNSURE
<222> LOCATION: (5)
<223> OTHER INFORMATION: 2-[(1-chloro-2-methylpropyloxy)carbonyl]
      -2-propylh ydrazine
<221> NAME/KEY: UNSURE
<222> LOCATION: (2)
<223> OTHER INFORMATION: Xaa=D-gamma-carboxyglutamic acid

<400> SEQUENCE: 4

Glu Xaa Val Val Pro
 1               5

<210> SEQ ID NO 5
<211> LENGTH: 5
<212> TYPE: PRT
<213> ORGANISM: Artificial Sequence
```

```
<220> FEATURE:
<223> OTHER INFORMATION: Description of Artificial Sequence:azapeptide
<221> NAME/KEY: MOD_RES
<222> LOCATION: (1)
<223> OTHER INFORMATION: ACETYLATION
<221> NAME/KEY: UNSURE
<222> LOCATION: (5)
<223> OTHER INFORMATION: 2-[(chloromethoxy)carbonyl]-2-propylhydrazine
<221> NAME/KEY: UNSURE
<222> LOCATION: (2)
<223> OTHER INFORMATION: Xaa=D-gamma-carboxyglutamic acid

<400> SEQUENCE: 5

Glu Xaa Val Val Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:azapeptide
<221> NAME/KEY: MOD_RES
<222> LOCATION: (1)
<223> OTHER INFORMATION: ACETYLATION
<221> NAME/KEY: UNSURE
<222> LOCATION: (5)
<223> OTHER INFORMATION: 2-[(1,2,2,2-tetrachloroethoxy)carbonyl]
     -2-propylhy drazine
<221> NAME/KEY: UNSURE
<222> LOCATION: (2)
<223> OTHER INFORMATION: Xaa=D-gamma-carboxyglutamic acid

<400> SEQUENCE: 6

Glu Xaa Val Val Pro
 1               5
```